US010941112B2

(12) United States Patent
Kurdyumov

(10) Patent No.: US 10,941,112 B2
(45) Date of Patent: *Mar. 9, 2021

(54) PHOTO-CROSSLINKER

(71) Applicant: Surmodics, Inc., Eden Prairie, MN (US)

(72) Inventor: Aleksey V. Kurdyumov, Lino Lakes, MN (US)

(73) Assignee: Surmodics, Inc., Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/414,315

(22) Filed: May 16, 2019

(65) Prior Publication Data
US 2019/0300474 A1    Oct. 3, 2019

Related U.S. Application Data

(63) Continuation of application No. 13/316,030, filed on Dec. 9, 2011, now Pat. No. 10,315,987.

(60) Provisional application No. 61/422,333, filed on Dec. 13, 2010.

(51) Int. Cl.
C07C 275/38    (2006.01)
C07C 271/28    (2006.01)

(52) U.S. Cl.
CPC .......... *C07C 275/38* (2013.01); *C07C 271/28* (2013.01)

(58) Field of Classification Search
None
See application file for complete search history.

(56) References Cited

U.S. PATENT DOCUMENTS

| | | |
|---|---|---|
| 3,352,896 A | 11/1967 | Dressler et al. |
| 3,395,116 A | 7/1968 | Dressler et al. |
| 3,869,527 A | 3/1975 | Hogberg |
| 4,045,426 A | 8/1977 | Sheppard et al. |
| 4,197,133 A | 4/1980 | Zweifel et al. |
| 4,954,534 A | 9/1990 | Yamamuro |
| 5,002,582 A | 3/1991 | Guire et al. |
| 5,069,719 A | 12/1991 | Ono |
| 5,154,182 A | 10/1992 | Moaddeb |
| 5,563,056 A | 10/1996 | Swan et al. |
| 5,637,460 A | 6/1997 | Swan et al. |
| 5,714,360 A | 2/1998 | Swan et al. |
| 5,942,555 A | 8/1999 | Swanson et al. |
| 6,022,307 A | 2/2000 | Salvati et al. |
| 6,077,698 A | 6/2000 | Swan et al. |
| 6,278,018 B1 | 8/2001 | Swan |
| 6,298,272 B1 | 10/2001 | Peterfeso et al. |
| 6,465,178 B2 | 10/2002 | Chappa et al. |
| 6,669,994 B2 | 12/2003 | Swan et al. |
| 6,849,639 B2 | 2/2005 | Dominguez et al. |
| 7,087,658 B2 | 8/2006 | Swan et al. |
| 7,144,573 B2 | 12/2006 | Guire et al. |
| 7,176,297 B2 | 2/2007 | Li et al. |
| 7,244,444 B2 | 7/2007 | Bates |
| 7,309,593 B2 | 12/2007 | Ofstead et al. |
| 7,348,055 B2 | 3/2008 | Chappa et al. |
| 7,529,592 B2 | 5/2009 | Cates et al. |
| 8,668,667 B2 | 3/2014 | Chappa |
| 8,889,760 B2 | 11/2014 | Kurdyumov et al. |
| 9,487,663 B2 | 11/2016 | Kurdyumov et al. |
| 9,994,721 B2 | 6/2018 | Kurdyumov et al. |
| 10,253,193 B2 | 4/2019 | Kurdyumov et al. |
| 10,315,987 B2 | 6/2019 | Kurdyumov |
| 10,745,573 B2 | 8/2020 | Kurdyumov |
| 2002/0004140 A1 | 1/2002 | Swan et al. |
| 2004/0137250 A1 | 7/2004 | Daniel et al. |
| 2007/0003707 A1 | 1/2007 | Guire et al. |
| 2009/0093550 A1 | 4/2009 | Rolfes et al. |
| 2010/0227077 A1 | 9/2010 | Wen et al. |
| 2011/0144373 A1 | 6/2011 | Swan et al. |
| 2011/0245367 A1 | 10/2011 | Kurdyumov et al. |
| 2012/0046384 A2 | 2/2012 | Kurdyumov et al. |
| 2012/0149934 A1 | 6/2012 | Kurdyumov |
| 2015/0166801 A1 | 6/2015 | Kurdyumov et al. |
| 2017/0022375 A1 | 1/2017 | Kurdyumov et al. |
| 2017/0281831 A1 | 10/2017 | Militello |
| 2018/0169305 A1 | 6/2018 | Slager et al. |
| 2018/0273773 A1 | 9/2018 | Kurdyumov et al. |
| 2019/0367748 A1 | 12/2019 | Kurdyumov |

FOREIGN PATENT DOCUMENTS

| | | |
|---|---|---|
| CN | 101602682 | 12/2009 |
| EP | 148787 | 7/1985 |
| EP | 1557413 | 7/2005 |
| EP | 2552927 | 3/2019 |

(Continued)

OTHER PUBLICATIONS

Sherwood et al., A three-dimensional osteochondral composite scaffold for articular cartilage repair, 2002, Biomaterials, 23, pp. 4739-4751 (Year: 2002).*
Andrianov, K A. et al., "Some Diketodicarboxylic Silicoorganic Acids," Journal of General Chemistry of the USSR, vol. 31, No. 1, (1961), pp. 218-221.
Andrianov, K. A. et al., "Acylation of Arylaliphatic Disiloxanes," Journal of General Chemistry of the USSR, vol. 29, (1959), pp. 2669-2672.
Braun, D. I. "Plastics," Concise Encyclopedia of Polymer Science and Engineering, (1990), pp. 462-464.
"Cas RN 41351-06-8," Nov. 16, 1984.
"CAS RN 41351-07-9," Nov. 16, 1984.
"CAS RN 41351-26-2," Nov. 16, 1984.
"CAS RN 730911-91-8," Aug. 22, 2004.
"CAS RN 767584-93-0," Oct. 22, 2004.

(Continued)

*Primary Examiner* — Kortney L. Klinkel
*Assistant Examiner* — Tori Strong
(74) *Attorney, Agent, or Firm* — Pauly, DeVries Smith & Deffner LLC

(57) ABSTRACT

Described herein is a linking agent that includes a polymeric or non-polymeric core molecule and one or more photoreactive groups covalently attached to the core molecule by one or more linking elements that include a urea linkage, a carbamate linkage, or a combination thereof.

8 Claims, No Drawings

(56) References Cited

FOREIGN PATENT DOCUMENTS

| | | |
|---|---|---|
| EP | 3581213 | 12/2019 |
| GB | 1021194 | 3/1966 |
| GB | 1406611 | 9/1975 |
| JP | S45030568 | 10/1970 |
| JP | S48029746 | 4/1973 |
| JP | 61192778 | 8/1986 |
| JP | 6429384 | 1/1989 |
| JP | H02187437 | 7/1990 |
| JP | 2002138283 | 5/2002 |
| JP | 2002322380 | 11/2002 |
| JP | 2007264291 | 10/2007 |
| JP | 2010519090 | 6/2010 |
| WO | 1997016544 | 5/1997 |
| WO | 2001044174 | 6/2001 |
| WO | 0248204 | 6/2002 |
| WO | 2003097117 | 11/2003 |
| WO | 2006135910 | 12/2006 |
| WO | 2007003507 | 1/2007 |
| WO | 2007/137794 | 12/2007 |
| WO | 2008022258 | 2/2008 |
| WO | 2011072199 | 6/2011 |
| WO | 2011123441 | 10/2011 |

OTHER PUBLICATIONS

"CAS RN 780693-90-5," Nov. 14, 2004.
"CAS RN 86967-57-9," Nov. 16, 1984.
Chekmacheva, et al., "Phosphorylated Derivatives of Hydroxybenzophenones," Zhurnal Obshchei Khimii, 1983, 53(2), pp. 281-285.
Chekmacheva, O. I. et al., "Phosphorylated Derivatives of Hydroxybenzophenones. I. Synthesis and Properties of Phosphorylated Derivatives of p-hydroxybenzophenone," Journal of General Chemistry of the USSR, vol. 53, No. 2, (1983), pp. 243-247.
Chekmacheva, O. I. et al., "Phosphorylated Hydroxybenzophenones. II. Synthesis and Properties of Phosphorylated o-hydroxybenzophenones," Journal of General Chemistry of the USSR, vol. 53, No. 4, (1983), pp. 653-655.
Chekmacheva, O.I. et al., "Phosphorylated Derivatives of Hydroxybenzophenones," Zhurnal Obshchei Khimii, 1983, 53(5), pp. 1028-1031.
"Communication Pursuant to Article 94(3) EPC," for European Patent Application No. 11713146.6 mailed on Jul. 2, 2015 (4 pages).
"Communication Pursuant to Article 94(3) EPC," for European Patent Application No. 11713146.6, mailed Apr. 3, 2017 (4 pages).
"Communication Pursuant to Article 94(3) EPC," for European Patent Application No. 11713146.6, mailed Dec. 18, 2017 (3 pages).
"Communication Pursuant to Article 94(3) EPC," for European Patent Application No. 11713146.6, mailed Jul. 7, 2014 (4 pages).
"Communication Pursuant to Rules 161(1) and 162 EPC," for European Patent Application No. 11713146.6, mailed Nov. 9, 2012 (2 pages).
"Decision of Rejection," for Japanese patent application No. 2013-502749 dated Aug. 30, 2016 (7 pages) with English Translation.
"Examination Report," for Brazilian Patent Application No. 112012024919-3, dated May 13, 2018 (14 pages) with English translation.
"Fifth Office Action," for Chinese Patent Application No. 201180021034.3, dated Sep. 12, 2018 (6 pages) with English Translation.
"File History," for U.S. Appl. No. 13/316,030, (445 pages).
"Final Office Action," for U.S. Appl. No. 12/965,020, dated Jul. 25, 2014 (13 pages).
"Final Office Action," for U.S. Appl. No. 13/074,537, dated Aug. 20, 2014 (10 pages).
"Final Office Action," for U.S. Appl. No. 14/541,768 dated Sep. 23, 2015 (14 pages).
"Final Office Action," for U.S. Appl. No. 15/283,818 dated Jul. 21, 2017 (12 pages).
"Final Office Action," from U.S. Appl. No. 12/965,020, dated Aug. 6, 2013, 13 pages.
"Final Rejection," for Chinese Patent Application No. 201180021034.3 dated Jan. 6, 2017 (14 pages) with English translation.
"First Examination Report," for Indian Patent Application No. 3124/KOLNP/2012 dated Oct. 27, 2017 (6 pages).
"First Office Action," for Chinese Patent Application No. 201180021034.3, dated Jun. 5, 2014, 21 pages with English translation.
"Fourth Office Action," for Chinese Patent Application No. 201180021034.3 dated Sep. 6, 2016 (10 pages) with English Translation.
George, Maurice H. et al., "The Synthesis of Precisely Structured Polyurethanes. Part 2. Chain Building Methodology," Journal of the Chemical Society, Perkin Transacti Ons 1, No. 12, (1996), pp. 1395-1401.
Harper, S. D. et al., "Intramolecular Oxidative Cyclization Reactions of Trivalent Phosphorus and Carbonyl Functions," Journal of the American Chemical Society, vol. 104, No. 9, (1982), pp. 2497-2501.
"International Preliminary Report on Patentability," for PCTUS2010059832, dated Jun. 21, 2012 (10 pages).
Ismail, Roshdy M. et al., "Uber die Herstellung und UV-Absorption einiger Siliciumester and Metalle enthaltender Benzophenon-Derivate," Zeitschrift Fuer Naturforschung, Teil B: Anorganische Chemie, Organische Chemie, vol. 25, (1970), pp. 14-18.
Li, Shen-Xin et al., "Degradation of Diphenylamine by Persulfate: Performance Optimization, Kinetics and Mechanism," Journal of Hazardous Materials 164 (2009) pp. 26-31.
Magano, Javier et al., "2-(Diethylamino)ethanethiol, a New Reagent for the Odorless Deprotection of Aromatic Methyl Ethers," J. Org. Chem. 2006, 71, 7103-7105.
"Non Final Office Action," for Russian Patent Application No. 2012144225, dated May 18, 2015 (6 pages) with English translation.
"Non Final Office Action," for Russian Patent Application No. 2012144225, dated Oct. 19, 2015 (6 pages) with English translation.
"Non-Final Office Action," for U.S. Appl. No. 12/965,020, dated Apr. 2, 2013 (97 pages).
"Non-Final Office Action," for Japanese Patent Application No. 2013-502749, dated Jan. 27, 2015 (8 pages) with English translation.
"Non-Final Office Action," for U.S. Appl. No. 13/074,537, dated May 22, 2014 (20 pages).
"Non-Final Office Action," for U.S. Appl. No. 12/965,020, dated Feb. 20, 2014 (16 pages).
"Non-Final Office Action," for U.S. Appl. No. 14/541,768, dated May 6, 2016 (11 pages).
"Non-Final Office Action," for U.S. Appl. No. 14/541,768, dated May 8, 2015 (14 pages).
"Non-Final Office Action," for U.S. Appl. No. 15/283,818, dated Dec. 1, 2016 (23 pages).
"Non-Final Office Action," for U.S. Appl. No. 15/994,206 dated Jul. 12, 2018 (19 pages).
"Notice of Allowance," for U.S. Appl. No. 14/541,768 dated Jul. 29, 2016 (10 pages).
"Notice of Allowance," for U.S. Appl. No. 14/541,768, dated Feb. 10, 2016 (7 pages).
"Notice of Allowance," for U.S. Appl. No. 15/994,206 dated Nov. 30, 2018 (10 pages).
"Notice of Allowance," For U.S. Appl. No. 13/074,537, dated Oct. 7, 2014 (15 pages).
"Notification for Patent Reexamination," for Chinese Patent Application No. 201180021034.3 dated Dec. 5, 2017 (16 pages) with English translation.
"Nucleophilic Substitution—SN1—Elimination," http://chemistry2.csudh.edu/rpendarvis/SN1Elim.html, 2001, pp. 1-7.
"Nucleophilic Substitution—SN2," http://chemistry2.csudh.edu/rpendarvis/SN2.html, 2001, pp. 1-6.
"Office Action Received," for Russian Application No. 2012144225, Corresponding U.S. Appl. No. 13/074,537, dated Dec. 19, 2012 (3 pages).
"Office Action Response," for Canadian Patent Application No. 2,794,795 filed Nov. 30, 2018 (7 pages).
"Office Action," for Canadian Patent Application No. 2,794,795 dated Feb. 9, 2017 (7 pages).

(56) References Cited

OTHER PUBLICATIONS

"Office Action," for Canadian Patent Application No. 2,794,795 dated Jul. 16, 2018 (3 pages).
"Office Action," for Canadian Patent Application No. 2,794,795 dated Mar. 11, 2019 (3 pages).
"Office Action," for Canadian Patent Application No. 2,794,795 dated Oct. 16, 2017 (4 pages).
"Office Action," for Japanese Patent Application No. 2013-502749, dated Jan. 5, 2016 (8 pages) with translation.
"Office Action," for Japanese Patent Application No. 2016-253675 dated Nov. 21, 2017 (12 pages) with English translation.
"Office Action," for Mexico Patent Application No. MX/a/2012/011061, dated Aug. 10, 2014 (1 page).
"Office Action," for Mexico Patent Application No. MX/a/2012/011061, dated May 7, 2015 (3 pages).
"Office Action," for Russian Patent Application No. 2012144225, dated Jan. 27, 2015 (8 pages) with English Translation.
"PCT International Search Report and Written Opinion," from International Application No. PCT/US2010/059832, corresponding to U.S. Appl. No. 61/285,345, dated Dec. 13, 2011, pp. 1-15.
"PCT International Search Report and Written Opinion," from International Application No. PCT/US2011/030319, corresponding to U.S. Appl. No. 61/422,333, dated Jul. 22, 2011, (15 pages).
"PCT Notification Concerning Transmittal of International Preliminary Report," from International Application No. PCT/US2011/030319, dated Oct. 11, 2012, (8 pages).
Pinkus, A. G. et al., "Reactions of Chlorosilanes and 5-chloro-2-hydroxybenzophenone," The Journal of Organic Chemistry, vol. 34, No. 4, (1969), pp. 1094-1097.
Pratt, Colin "Applications of Conducting Polymers," http://homepage.ntlworld.com/colin.pratt/applcp.htm, (2009), pp. 1-7.
"Response Final Office Action," for U.S. Appl. No. 14/541,768, dated Sep. 23, 2015 and filed with the USPTO Oct. 22, 2015 (3 pages).
"Response to Communication Pursuant to Article 94(3) EPC," for European Patent Application No. 11713146.6, filed with the EPO Apr. 6, 2018 (80 pages).
"Response to Communication Pursuant to Article 94(3) EPC," for European Patent Application No. 11713146.6, filed with the EPO Jul. 31, 2017 (11 pages).
"Response to Communication Pursuant to Article 94(3) EPC," for European Patent Application No. 11713146.6, dated Jul. 2, 2015 and filed with the EPO Dec. 24, 2015 (13 pages).
"Response to Communication Pursuant to Article 94(3) EPC," for European Patent Application No. 11713146.6, mailed Jul. 7, 2014 and filed with the EPO Dec. 30, 2014 (14 pages).
"Response to Communication Pursuant to Rules 161(1) and 162 EPC," for European Patent Application No. 11713146.6, mailed Nov. 9, 2012 and filed with the EPO Apr. 5, 2013 (12 pages).
"Response to Final Office Action," for U.S. Appl. No. 13/074,537, dated Aug. 20, 2014 and filed with the USPTO Sep. 18, 2014 (5 pages).
"Response to Final Office Action," for U.S. Appl. No. 15/283,818, dated Jul. 21, 2017 and filed with the USPTO Oct. 12, 2017 (5 pages).
"Response to First Examination Report," for Indian Patent Application No. 3124/KOLNP/2012 filed with the Indian Patent Office Apr. 25, 2018 (22 pages).
"Response to First Office Action," for Chinese Patent Application No. 201180021034.3, dated Jun. 5, 2014 and filed with CIPO Nov. 27, 2014 (35 pages) with English translation.
"Response to Non Final Office Action," for U.S. Appl. No. 15/994,206, filed with the USPTO Nov. 12, 2018 (8 pages).
"Response to Non-Final Office Action," for U.S. Appl. No. 13/074,537, dated May 22, 2014 and filed with the USPTO Jul. 16, 2014 (7 pages).
"Response to Non-Final Office Action," for U.S. Appl. No. 14/541,768 dated May 6, 2016 and filed with the USPTO Jul. 12, 2016 (10 pages).
"Response to Non-Final Office Action," for U.S. Appl. No. 14/541,768, dated May 8, 2015 and filed with the USPTO Aug. 10, 2015 (13 pages).
"Response to Non-Final Office Action," for U.S. Appl. No. 15/283,818, dated Dec. 1, 2016 and filed with the USPTO Mar. 28, 2017 (9 pages).
"Response to Office Action," for Canadian Patent Application No. 2,794,795 filed with CIPO dated Apr. 12, 2018 (22 pages).
"Response to Office Action," for Canadian Patent Application No. 2,794,795 filed with CIPO dated Jul. 27, 2017 (19 pages).
"Restriction Requirement Received," dated Jan. 16, 2013 in co-pending U.S. Appl. No. 12/965,020, "Water-Soluble Degradable Photo-Crosslinker," (6 pages)., 6.
Schilling, Jansen H. et al., "Syntheses of Styrene and Butadien Cyclosiloxan Block Copolymer Having UV Absorber Residues," Acta Polymerica, 1989, 40(2), pp. 116-121.
"Second Office Action," for China Patent Application No. 201180021034.3, dated Mar. 26, 2015 (15 pages) including English translation.
Segal, John A. "Aromatic Polyether Synthesis via Activated Substitution in a Ruthenium(II) Complex of p-Dichlorobenzene," Journal of the Chemical Society, Chemical Communications, No. 19, (1985), pp. 1338-1339.
"Selected Aspects of Organosilicon Chemistry," Chapter 9, (2006), pp. 1-5.
Shin, Kwanghee A. et al., "Pathway and Evolutionary Implications of Diphenylamine Biodegradation by *Burkholderia* sp. Strain JS667," Applied and Environmental Microbiology, vol. 75, No. 9, May 2009, pp. 2694-2704.
"Silane Chemistry Primer," Dow Corning, (1995), pp. 1-4.
Singh, M. S. et al., "Synthesis and spectroscopic studies of 2-(N-salicylidene)-5-chlorobenzophenone derivatives of organosilicon(IV)," Phosphorus, Sulfur and Silicon and the Related Elements, vol. 130, (1997), pp. 147-153.
"Third Office Action," for Chinese Patent Application No. 201180021034.3, dated Dec. 15, 2015 (20 pages) including English translation.
"Third Office Action," for Mexican Patent Application No. MX/a/2012/011061, dated Nov. 8, 2015 (1 page).
Vysokomolekulyarnye Soedineniya, 1959, 1, pp. 704-710.
Wiese, Dietmar et al., "1,3-Bis(2-benzoylphenyl)-1,1,3,3-Tetramethyldisiloxan," Chemische Berichte, vol. 120, No. 6, (1987), pp. 873-878.
Zhurnal Obshchei Khimii, 1959, 20, pp. 2702-2706.
"Extended European Search Report," for European Patent Application No. 19161702.6 dated Sep. 5, 2019 (6 pages).
"Non-Final Office Action," for U.S. Appl. No. 16/378,222 dated Oct. 21, 2019 (18 pages).
"Office Action," for Japanese Patent Application No. 2018154782 dated Jul. 2, 2019 (6 pages) With English Translation.
"Response to Office Action," for Canadian Patent Application No. 2,794,795 filed Jul. 24, 2019 (6 pages).
"Notice of Allowance," for U.S. Appl. No. 16/378,222 dated Apr. 8, 2020 (10 pages).
"Response to Non-Final Office Action," for U.S. Appl. No. 16/378,222 filed via EFS-web dated Mar. 23, 2020 (7 pages).
"Response to Extended European Search Report," for European Patent Application No. 19161702.6 filed Jun. 16, 2020 (6 pages).

\* cited by examiner

PHOTO-CROSSLINKER

This application is a continuation of U.S. application Ser. No. 13/316,030, filed Dec. 9, 2011, which claims the benefit of U.S. Provisional Application No. 61/422,333, filed Dec. 13, 2010, the contents of which are herein incorporated by reference in their entireties.

TECHNICAL FIELD

The present invention relates to a linking agent having one or more photoactivatable groups.

BACKGROUND OF THE INVENTION

Photochemically reactive functional groups ("photoreactive groups") are functional groups that, when exposed to an appropriate energy source, undergo a transformation from an inactive state (i.e., ground state) to a reactive intermediate capable of forming covalent bonds with appropriate materials. Photoreactive groups can be used, for instance, to derivatize a target molecule (e.g., thermochemically), in order to then photochemically attach the derivatized target molecule to a surface. Photoreactive groups can also be used as photoinitiators for polymerization reactions.

SUMMARY OF THE INVENTION

Described herein is a linking agent that includes a polymeric or non-polymeric core molecule and one or more photoreactive groups covalently attached to the core molecule by one or more linking elements that include a urea linkage, a carbamate linkage, or a combination thereof.

In one embodiment, the linking agent can be represented by the formula:

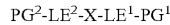

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof benzene or a derivative thereof; or a combination thereof.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

Described herein is a linking agent. The linking agent includes a core, one or more photoreactive groups and one or more linking elements configured to operably attach one or more photoreactive groups to the core.

In some instances, it may be desirable to include one or more bioactive agents in a surface coating. In one embodiment, the linking agent can be used for delivery of one or more bioactive agents. For example, the linking agent may be suitable for use as a drug delivery coating, particularly for bioactive agents that can tolerate (e.g., remain effective) exposure to ultra-violet radiation.

In one embodiment, one or more photoreactive groups of the linking agent is used as an initiator for photopolymerization. In one embodiment, the linking agent is used in connection with a composition that is capable of in situ polymerization.

In another embodiment, the linking agent can be used in the generation of grafts for tissue engineering. For example, the linking agent can be used to generate a three dimensional structure, sometimes referred to as a polymeric scaffolding or extracellular matrix, for cell attachment and migration. The polymeric scaffolding can be used in connection with tissue engineering technology for the repair and/or replacement of portions of or entire tissues and/or organs (e.g., bone, cartilage, blood vessels, bladder, etc Linking Agent As discussed above, the linking agent includes a core with one or more photoreactive groups attached to the core by a linking element. In another embodiment, the linking agent includes two or more, or a plurality of photo reactive groups. In one embodiment, the linking agent includes a polymeric core molecule. In another embodiment, the linking agent includes a non-polymeric core molecule. The term "linking element" as used herein, refers to a segment configured to connect one part of the linking agent to another, for example, to connect one or more photo reactive groups to the core.

A linking agent can be generally represented by the formula:

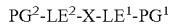

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof benzene or a derivative thereof; or a combination thereof.

As shown in this and other formulae contained herein, the two or more photoreactive groups ($PG^1$ and $PG^2$) are discrete. As used herein, the term "discrete" means that the two or more photoreactive groups are distinct from each other, as compared to a bifunctional photoreactive agent, that can include two or more photoreactive moieties, such as a conjugated cyclic diketone wherein each ketone group of the diketone is adapted to serve as a photoreactive moiety capable of being activated in order to provide a free radical. It is also understood that the first and second photoreactive groups and/or the first and second linkers may or may not be the same. For example, in one embodiment, the photoreactive groups ($PG^1$ and $PG^2$) are the same or identical. In another embodiment, the photoreactive groups ($PG^1$ and PG²) are not the same. In one embodiment, the linking elements (LE¹ and LE²) are the same or identical. In another embodiment, the linking elements (LE¹ and LE²) are not the same. In one embodiment, the photoreactive groups include one or more first photoreactive groups adapted to attach the linking agent to a surface and one or more second photoreactive groups adapted to initiate photopolymerization.

In a more particular embodiment, the linking agent can be represented by the following formula:

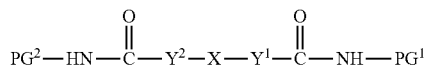

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $Y^1$ and $Y^2$ are, independently, O or N, wherein N can be a secondary amine (—NH—) or a tertiary amine (—NR—) in which R can be, independently, hydrogen, alkyl or aryl, including, but not limited to cyclic, linear or branched, saturated or unsaturated, aromatic or heteroaromatic, or a combination thereof and X represents a core molecule, which can be either polymeric or non-polymeric, including, but not limited to a hydrocarbon, including a hydrocarbon that is linear, branched, cyclic, or a combination thereof aromatic, non-aromatic, or a combination thereof; monocyclic, polycyclic, carbocyclic, heterocyclic, or a combination thereof benzene or a derivative thereof; or a combination thereof.

In one embodiment, the linking element includes one or more carbamate linkages.

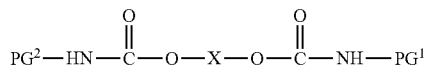

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof monocyclic, polycyclic, carbocyclic, heterocyclic, or a combination thereof benzene or a derivative thereof or a combination thereof.

In another embodiment, the linking element includes one or more urea linkages.

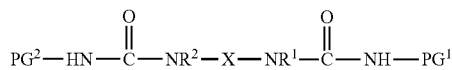

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $R^1$ and $R^2$, independently, can be hydrogen, alkyl or aryl, including, but not limited to cyclic, linear or branched, saturated or unsaturated, aromatic or heteroaromatic, or a combination thereof and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof benzene or a derivative thereof or a combination thereof. In one embodiment, $R^1$ and/or $R^2$ can include one or more photoreactive groups In another embodiment, the linking agent can be represented by the formula:

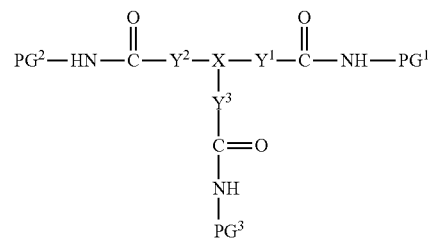

wherein $PG^1$, $PG^2$ and $PG^3$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $Y^1$, $Y^2$ and $Y^3$ are, independently, O or N, wherein N can be a secondary amine (—NH—) or a tertiary amine (—NR—) in which R can be, independently, hydrogen, alkyl or aryl, including, but not limited to cyclic, linear or branched, saturated or unsaturated, aromatic or heteroaromatic, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof benzene or a derivative thereof; or a combination thereof.

In another embodiment, the linking agent can be represented by the formula:

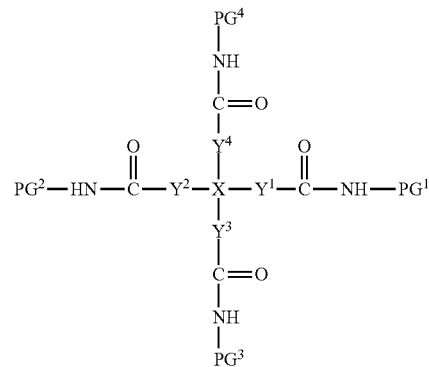

wherein $PG^1$, $PG^1$, $PG^3$ and $PG^4$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $Y^1$, $Y^2$, $Y^3$ and $Y^4$ are, independently, O or N, wherein N can be a secondary amine (—NH—) or a tertiary amine (—NR—) in which R can be, independently, hydrogen, alkyl or aryl, including, but not limited to cyclic, linear or branched, saturated or unsaturated, aromatic or heteroaromatic, or a combination thereof and X represents a core molecule, which can be either polymeric or non-polymeric, including, but not limited to a hydrocarbon, including a hydrocarbon that is linear, branched, cyclic, or a combination thereof aromatic, non-aromatic, or a combination thereof; monocyclic, polycyclic, carbocyclic, heterocyclic, or a combination thereof benzene or a derivative thereof; or a combination thereof.

One specific embodiment can be represented by the following formula:

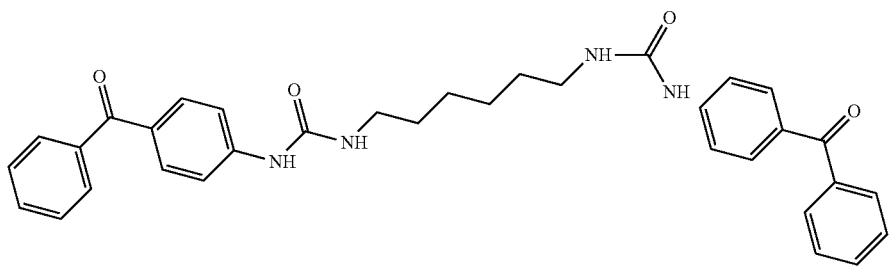

Another specific embodiment can be represented by the following formula:

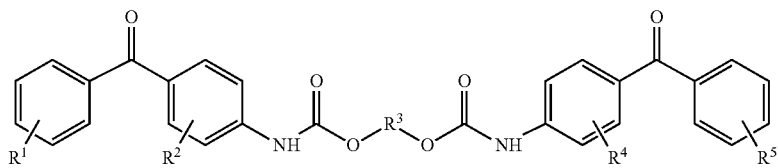

wherein $R^1$, $R^2$, $R^4$ and $R^5$ are independently halo, alkyl, alkaryl, aralkyl, —OH, —NH$_2$ and —SH; and $R^3$ is chosen from alkylene, arylene, alkarylene, and arylalkylene Another specific embodiment can be represented by the following formula:

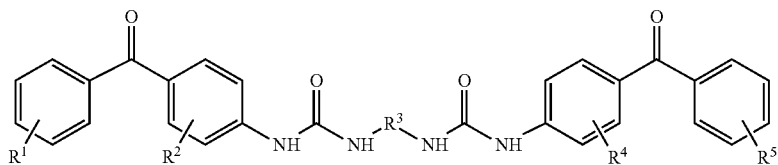

wherein $R^1$, $R^2$, $R^4$ and $R^5$ are independently halo, alkyl, alkaryl, aralkyl, —OH, —NH$_2$ and —SH; and $R^3$ is chosen from alkylene, arylene, alkarylene, and arylalkylene Photoreactive Groups As used herein, the term "photoreactive group" refers to a molecule having one or more functional groups that are capable of responding to specific applied external stimuli to undergo active specie generation and form a covalent bond with an adjacent chemical structure, which can be provided by the same or a different molecule. Photoreactive groups are those groups of atoms in a molecule that retain their covalent bonds unchanged under conditions of storage but that, upon activation by an external energy source, form one or more covalent bonds with other molecules. In one embodiment, the photoreactive groups can generate active species such as free radicals upon absorption of electromagnetic energy. Photoreactive groups can be chosen to be responsive to various portions of the electromagnetic spectrum, and photoreactive groups that are responsive to ultraviolet and visible portions of the spectrum and are referred to herein as "photochemical groups" or "photogroups." Photogroups are described, for example, in U.S. Pat. No. 5,002,582, the disclosure of which is incorporated herein by reference.

In one embodiment, the photoreactive groups include photoreactive aryl ketones, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. One example includes thioxanthone, and its derivatives, having excitation energies greater than about 360 nm.

The functional groups of such ketones are readily capable of undergoing the activation/inactivation/reactivation cycle described herein. Benzophenone is one example of a photoreactive moiety that is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are subject to multiple reactivation in water and may increase coating efficiency.

The azides constitute one class of photoreactive groups and include derivatives based on arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include derivatives of diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH═C═O) such as ketene and diphenylketene.

Upon activation of the photoreactive groups, the linking agents are covalently bound to each other, to other molecules, or to a surface by covalent bonds through residues of the photoreactive groups. Exemplary photoreactive groups, and their residues upon activation, are shown as follows.

| Photoreactive Group | Residue Functionality |
| --- | --- |
| aryl azides | amine (R—NH—R') |
| acyl azides | amide (R—CO—NH—R') |
| azidoformates | carbamate (R—O—CO—NH—R') |
| sulfonyl azides | sulfonamide (R—$SO_2$—NH—R') |
| phosphoryl azides | phosphoramide (($RO)_2$PO—NH—R') |
| Diazoalkanes | new C—C bond |
| diazoketones | new C—C bond and ketone |
| diazoacetates | new C—C bond and ester |
| beta-keto-alpha-diazoacetates | new C—C bond and beta-ketoester |
| aliphatic azo | new C—C bond |
| Diazirines | new C—C bond |
| Ketenes | new C—C bond |
| photoactivated ketones | new C—C bond and alcohol |

Photoinitiation of free radical polymerization can take place via various mechanisms, including photochemical intramolecular photocleavage, hydrogen abstraction, and redox reactions. In one embodiment, photoinitiation takes place by hydrogen abstraction from the polymerizable groups.

Intramolecular photocleavage involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone. For example, in one embodiment wherein the linking agent is provided in the form of a quinone having adjacent carbonyl groups (e.g., camphorquinone), photoinitiation takes place via intramolecular bond cleavage.

A second mechanism, hydrogen abstraction, can be either intra- or intermolecular in nature. A system employing this mechanism can be used without additional energy transfer acceptor molecules and by nonspecific hydrogen abstraction. However, this system is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone and camphorquinone.

A third mechanism involves photosensitization reactions utilizing photoreducible or photo-oxidizable dyes. In most instances, photoreducible dyes are used in conjunction with a reductant, typically a tertiary amine. The reductant intercepts the induced triplet producing the radical anion of the dye and the radical cation of the reductant.

In one embodiment, photoinitiation generates active species such as free radicals, including nitrenes, carbenes, and excited states of ketones upon absorption of electromagnetic energy. This excited photoinitiator in turn abstracts hydrogen atoms from available sources in proximity to the photoinitiator, e.g., polymerizable species, applied to the primed surface. This hydrogen abstraction thus generates a free radical site within the polymerizable species from which polymerization can proceed.

A typical free radical polymerization includes four steps: initiation, propagation, and termination. In initiation, a free radical derived from an initiator adds to a monomer molecule to form an active center. Other initiating reactions include addition to the head of the molecule or hydrogen abstraction, and the reaction mechanism depends upon the structures of the radical and monomer. The propagation or growth reaction includes of the rapid addition of monomer molecules to the radical species. The most common mechanism of propagation occurs in head-to-tail fashion. However, propagation may also occur in head-to-head, tail-to-head, and tail-to-tail modes. In termination, the polymer chain stops growing by the destruction of propagating radicals. Normally, in the absence of species that destroy radicals, chain termination occurs by bimolecular interaction of radicals (e.g., radical combinations or di sproportionation).

In one embodiment, the linking agent includes a conjugated cyclic diketone having attached thereto, either directly or indirectly, one or more substituents including negatively charged groups, and wherein each ketone group of the diketone is adapted to serve as a photoreactive moiety capable of being activated in order to provide a free radical. In one embodiment, the conjugated cyclic diketone is a quinone selected from substituted and unsubstituted benzoquinone, camphorquinone, naphthoquinone, and anthraquinone.

Core

The linking agent described herein can include a polymeric or non-polymeric core molecule. In one embodiment, the linking agent includes a polymeric core, which can be a naturally occurring polymer or a synthetic polymer. Non-polymeric core molecules may be desirable in some instances due to their increased coating density, structural stability, ease of manufacture, and reduced cost. Suitable core molecules can be non-polymeric with a low molecular weight (e.g., 100-1000 MW). In one embodiment, the non-polymeric core molecule is a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or combinations thereof.

In one embodiment, the core molecule functions as a spacer, to increase the distance between two or more photoreactive groups. For example, to reduce steric hindrance that could interfere with the ability of one or more photoreactive groups to form covalent bonds with a support surface, or from serving as a photoinitiator for polymerization. As described herein, it is possible to vary the distance between the photoreactive groups, for example, by increasing or decreasing the spacing between one or more photoreactive groups.

Surface Modification

In one embodiment, the linking agent is used to form a coating on a substrate surface. The coating can be formed in any suitable manner, e.g., by simultaneous or sequential attachment of the linking agent and chemical compounds (e.g., molecules bearing polymerizable groups) to a support surface. In one embodiment, the method involves a two step process, involving sequential steps in which linking agent is first attached to the surface, after which compounds are polymerized thereon using the photoinitiator of the attached agent. One advantage of a sequential approach is that photopolymerization of this sort allows the generation of thin polymer layers on the support surface. The resultant polymer layer is typically highly adherent, uniform in thickness, and is highly durable. Moreover, solutions used to form the polymer layer can be applied (e.g., via in solution application, dip coating, spray coating, knife coating, and roller coating) to any suitable support surface of any surface morphology. The resultant polymer layer, in turn, can be adapted to cover irregular surfaces as well as smooth, relatively uniform surfaces. The polymerizable species can also be attached to the support surface simultaneously with the linking agent, by providing suitable reaction conditions to allow such simultaneous attachment of the linking agent and polymerization of the polymerizable species.

The photoinitiator group (i.e., the second photoreactive group) can be identical to, or different from, the first photoreactive group used to attach the linking agent to a support surface. In one embodiment, the first and second photoreactive groups are adapted to be independently activated by light of different wavelengths (e.g., ultraviolet light versus visible light).

Upon activation of the photoreactive groups in the presence of a support surface, the second photoreactive group(s) remain unbound to the support surface and revert to their inactive state in order to serve as photoinitiator groups. While not intending to be bound by theory, it appears that the ability of a photoreactive group to remain unbound (and hence serve as a photoinitiator) is a factor, at least in part, of various reaction conditions (e.g., time and intensity of illumination wavelength, reagent concentration, etc.) and/or restrictions imposed by the size and/or structure of the linking agent itself. The photoinitiator thus remains available to be subsequently activated by a suitable energy source, and thereby initiate photopolymerization.

In one embodiment, the linking agents described herein are applied to a surface having carbon-hydrogen bonds with which the photoreactive groups can react to immobilize the linking agents. In one embodiment, the support surface provides abstractable hydrogen atoms suitable for covalent bonding with the activated group. In another embodiment, the surface can be modified (e.g., by pretreatment with a suitable reagent) to provide abstractable hydrogen atoms on the surface.

The method described herein is suitable for use in connection with a variety of support surfaces, including hydrogel polymers, silicone, polypropylene, polystyrene, poly(vinyl chloride), polycarbonate, poly(methyl methacrylate), parylene and any of the numerous organosilanes used to pretreat glass or other inorganic surfaces. The photoreactive linking agents can be applied to surfaces in any suitable manner (e.g., in solution or by dispersion), then photoactivated by uniform illumination to immobilize them to the surface. Examples of suitable hydrogel polymers are selected from silicone hydrogels, hydroxyethylmethacrylate polymers, and glyceryl methacrylate polymers.

Other suitable surface materials include polyolefins, polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics. See generally, "Plastics," pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Such materials can be used to fabricate a number of devices capable of being provided, either before, during and/or after their fabrication, with a polymer layer. Implant devices are one general class of suitable devices, and include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; ophthalmic devices such as lenses and glaucoma drain shunts; and other catheters, synthetic prostheses and artificial organs. Other suitable biomedical devices include dialysis tubing and membranes, blood oxygenator tubing and membranes, blood bags, sutures, membranes, cell culture devices, chromatographic support materials, biosensors, and the like.

Surface modification can be achieved using photopolymerization (e.g., by free radical polymerization). In accordance with the present method, a selected surface is contacted with a linking agent, as described above. During and/or after application of the linking agent, the surface is illuminated with UV light of the appropriate wavelength, thereby activating the photoreactive groups. The linking agent is thus immobilized to the surface, by means of the first photoreactive groups (with the second photoreactive groups reverting to inactive form), and excess linking agent can then be optionally washed away, leaving a surface primed with a base layer of linking agent.

The linking agent can be applied to the surface of interest in any suitable manner. For example, the linking agent can be applied by dip coating or by dispersing the agent on the surface (for example, by spray coating). Suitable methods of application include application in solution, dip coating, spray coating, knife coating, and roller coating. In one embodiment, the linking agent is applied to the surface via spray coating, as this application method provides increased density of the linking agent on the support surface, thereby improving grafting durability.

In the sequential approach described herein, a solution containing polymerizable compounds can be applied to a primed surface. The solution can be illuminated in situ to activate the second photoreactive group(s) that serve as a photoinitiator(s), thus initiating free radical polymerization via hydrogen abstraction. In one embodiment, photopolymerization takes place in an inert atmosphere, since oxygen interferes with free radical polymerization. Deoxygenation can take place using an inert gas such as nitrogen.

Once the system has been deoxygenated, the surface can again be illuminated with UV light of the appropriate wavelength. This second illumination thus activates the second photoreactive group(s) serving as a photoinitiator(s) of free radical polymerization. In one embodiment, illumination generates the excited state of the photoreactive group, allowing the excited molecule to abstract hydrogen from available sources, e.g., molecules bearing polymerizable groups. Such hydrogen abstraction generates a free radical site, from which polymerization can proceed.

The method includes steps of providing a support surface and applying a linking agent to the support surface. In one embodiment, the method further includes a step of illuminating the linking agent to photochemically attach the linking agent to the surface. In one embodiment, the method further includes a step of providing a plurality of molecules bearing free radical polymerizable groups and illuminating the molecules bearing polymerizable groups and the linking agent to initiate polymerization of the molecules bearing polymerizable groups on the support surface.

In one embodiment the linking agent is used in connection with a plurality of molecules, each bearing one or more polymerizable groups. In accordance with this embodiment, the photoreactive group serves as an initiator to initiate polymerization of the polymerizable groups. As used herein, "polymerizable group" refers to a group that is adapted to be polymerized by initiation via free radical generation, and by photoinitiators activated by visible or long wavelength ultraviolet radiation.

A variety of polymerizable compounds are suitable for use as with the linking agent described herein. In one embodiment, the polymerization products (e.g., a polymer layer resulting from free radical polymerization) is hydrophilic or is capable of being modified to provide hydrophilic characteristics at appropriate reaction conditions (e.g., pH). Moreover, the polymerizable groups of such compounds can include those adapted to participate in free-radical polymerization. In one embodiment, compounds include at least one free-radical polymerizable component (e.g., a vinyl group), and at least one functional group with a high affinity for water. Such functional groups with a high affinity for water can be negatively charged, positively charged, or electrically neutral.

Suitable polymerizable compounds are selected from monomeric polymerizable molecules (e.g., organic monomers), and macromeric polymerizable molecules (e.g., organic macromers). As used herein, "macromer" shall refer to a macromolecular monomer having a molecular weight of about 250 to about 25,000, and from about 1,000 to about 5,000.

Suitable polymerizable compounds can contain electrically neutral hydrophilic functional units, for example, acrylamide and methacrylamide derivatives. Examples of suitable monomers containing electrically neutral hydrophilic structural units include acrylamide, methacrylamide, N-alkylacrylamides (e.g., N,N-dimethylacrylamide or methacrylamide, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate).

Alternatively, suitable polymerizable compounds containing electrically neutral hydrophilic functional units include molecules whose polymers, once formed, can be readily modified (e.g., hydrolyzed by the addition of ethylene oxide) to provide products with enhanced affinity for water. Examples of suitable monomers of this type include glycidyl acrylate or methacrylate, whose polymers bear epoxy groups that can be readily hydrolyzed to provide glycol structures having a high affinity for water.

Examples of suitable monomeric polymerizable molecules that are negatively charged at appropriate pH levels include acrylic acid, methacrylic acid, maleic acid, fumaric acid, itaconic acid, AMPS (acrylamidomethylpropane sulfonic acid), vinyl phosphoric acid, vinylbenzoic acid, and the like.

Alternatively, suitable monomeric polymerizable molecules that are negatively charged at appropriate pH levels include molecules whose polymers, once formed, can be readily modified (e.g., by hydrolysis via the addition of ethylene oxide) to provide products with enhanced affinity for water. Examples of suitable monomers of this type include maleic anhydride, whose polymers bear anhydride groups that can be readily hydrolyzed to provide carboxylic acid groups, or can be readily reacted with amines to provide amide/acid structures with high affinity for water, and polymerized vinyl esters.

Examples of suitable monomeric molecules that are positively charged at appropriate pH levels include 3-aminopropylmethacrylamide (APMA), methacrylamidopropyltrimethylammonium chloride (MAPTAC), N,N-dimethylaminoethylmethacrylate, N,N-diethylaminoethylacrylate, and the like.

Alternatively, suitable positively charged monomeric polymerizable molecules include those molecules that can be readily modified (e.g., by hydrolysis via the addition of ethylene oxide) to provide products with enhanced affinity for water as well as a positive charge, e.g., glycidyl methacrylate whose polymeric products can be reacted with amines (e.g., ethylamine), to provide hydroxyamino compounds. In some cases, these materials will contain a structural unit with an inherent positive charge, as for example with fully quaternized ammonium structures. In other cases, the positively charged structural unit will exist at certain pH values, particularly at acidic pH values.

In an alternative embodiment, the polymerizable compounds include macromeric polymerizable molecules. Suitable macromers can be synthesized from monomers such as those illustrated above. According to one embodiment, polymerizable functional components (e.g., vinyl groups) of the macromer can be located at either terminus of the polymer chain, or at one or more points along the polymer chain, in a random or nonrandom structural manner.

The number of free-radical polymerizable groups per molecule can be varied according to the application. For example, a macromer with just one free-radical polymerizable unit can be used. In other instances, however, a macromer with more than one, e.g., two or more polymerizable units per macromer can be used. Additionally, the macromer can contain structural features to provide improved affinity for water in a manner typically unavailable in small molecule structures (e.g., hydrophilic poly(ethylene glycol) materials).

Examples of suitable macromeric polymerizable compounds include methacrylate derivatives, monoacrylate derivatives, and acrylamide derivatives. Macromeric polymerizable compounds include poly(ethylene glycol) monomethyacrylate, methoxypoly(ethylene glycol)

monomethacrylate, poly(ethylene glycol)monoacrylate, monomethyacrylamidopoly(acrylamide), poly(acrylamide-co-3-methacrylamidopropylacrylamide), poly(vinylalcohol)monomethacrylate, poly(vinylalcohol)monoacrylate, poly(vinylalcohol)dimethacrylate, and the like.

Such macromers can be prepared, for instance, by first synthesizing a hydrophilic polymer of the desired molecular weight, followed by a polymer modification step to introduce the desired level of polymerizable (e.g., vinyl) functional units. For example, acrylamide can be copolymerized with specific amounts of 3-aminopropylmethacrylamide comonomer, and the resulting copolymer can then be modified by reaction with methacrylic anhydride to introduce the methacrylamide functional units, thereby producing a useful macromer.

Poly(ethylene glycol) of a desired molecular weight can be synthesized or purchased from a commercial source, and modified (e.g., by reaction with methacryloyl chloride or methacrylic anhydride) to introduce the terminal methacrylate ester units to produce a suitable macromer. Some applications can benefit by use of macromers with the polymerizable units located at or near the terminus of the polymer chains, whereas other uses can benefit by having the polymerizable unit(s) located along the hydrophilic polymer chain backbone.

Such monomeric and macromeric polymerizable molecules can be used alone or in combination with each other, including for instance, combinations of macromers with other macromers, monomers with other monomers, or macromers combined with one or more small molecule monomers capable of providing polymeric products with the desired affinity for water. Moreover, the above polymerizable compounds can be provided in the form of amphoteric compounds (e.g., zwitterions), thereby providing both positive and negative charges.

EXAMPLES

Example 1: Preparation of a Linking Agent with a Urea Linkage

Anhydrous methylene chloride (10 mL) was added to a 25 mL round-bottom flask equipped with a magnetic stir bar which contained 4-isocyanatobenzophenone (0.988 g) under inert atmosphere. The starting material did not fully dissolve. 1,6-hexanediamine (0.254 g) and DMAP (90 mg) was added to the reaction mixture. The reaction mixture was allowed to stir under inert atmosphere for 4 days. The product was collected by vacuum filtration and washed with methylene chloride (5×10 mL). ¹H NMR confirmed the structure. The product was not further purified.

Example 2: Preparation of a Linking Agent with a Carbamate Linkage 4-isocyantobenzophenone (2 equiv.) is dissolved in methylene chloride in a round-bottom flask equipped with a magnetic stir bar and under nitrogen. DMAP (0.1 equiv.) is added to the reaction flask. This is followed by addition of 1,6-octanediol (1 equiv). The reaction mixture is allowed to stir at room temperature for 16 hours. It is then poured into water and washed with 0.1 N HCL until slightly acidic, water (2 times) and brine. The organic portion is dried over NaSO₄ and solvent is evaporated in vacuo. The crude product is recrystallized from methylene chloride.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of the metal injection molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

What is claimed is:

1. A medical device comprising
   a substrate comprising a substrate surface;
   a coating layer disposed over the substrate surface, the coating layer comprising the linking agent comprising a compound having the structure;

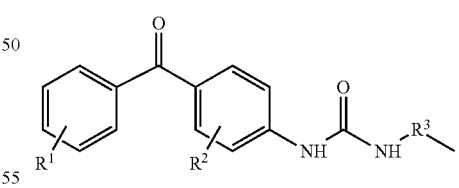

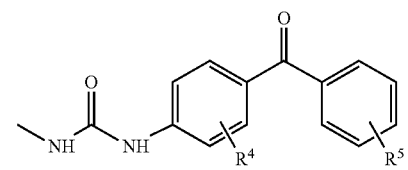

wherein R¹, R², R⁴ and R⁵ are independently hydrogen; and R³ is C1-C6 alkyl.

2. The medical device of claim 1, the linking agent having the structure:

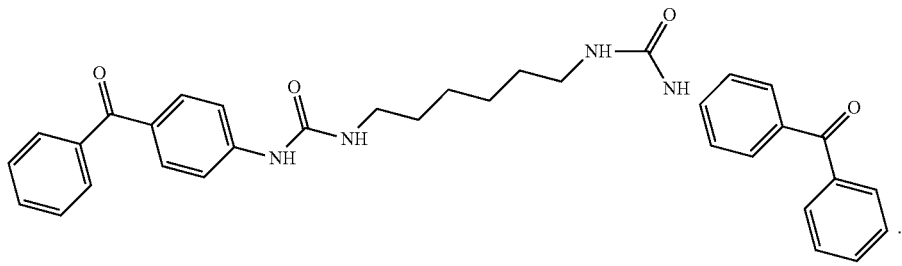

3. The medical device of claim 1, comprising a vascular device.

4. The medical device of claim 1, comprising a catheter.

5. The medical device of claim 1, the substrate comprising at least one selected from the group consisting of a hydrogel polymer, a silicone, a polypropylene, a polystyrene, a poly(vinyl chloride), a polycarbonate, a poly(methyl methacrylate), and a parylene.

6. The medical device of claim 1, the substrate comprising at least one selected from the group consisting of a polyolefin, a polystyrene, a poly(methyl)methacrylate, a polyacrylonitrile, a poly(vinylacetate), a poly(vinyl alcohol), a polyoxymethylene, a polyamide, a polyimide, a polyurethane, a phenolic, an amino-epoxy resin, and a polyester.

7. The medical device of claim 1, the coating layer comprising a three-dimensional scaffolding structure.

8. The medical device of claim 1, wherein $R^3$ is either a C5 alkyl or a C6 alkyl.

* * * * *